United States Patent
Fan et al.

(10) Patent No.: US 8,343,050 B2
(45) Date of Patent: Jan. 1, 2013

(54) FEEDBACK IN MEDICAL ULTRASOUND IMAGING FOR HIGH INTENSITY FOCUSED ULTRASOUND

(75) Inventors: Liexiang Fan, Sammamish, WA (US); Kevin Sekins, Yallow Point, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 706 days.

(21) Appl. No.: 12/435,196

(22) Filed: May 4, 2009

(65) Prior Publication Data
US 2010/0280373 A1 Nov. 4, 2010

(51) Int. Cl.
*A61B 8/00* (2006.01)
(52) U.S. Cl. ......... 600/437; 600/407; 600/438; 600/439
(58) Field of Classification Search ................. 600/437, 600/407, 438, 439
See application file for complete search history.

(56) References Cited

U.S. PATENT DOCUMENTS

| | | | |
|---|---|---|---|
| 5,107,837 A | 4/1992 | Ophir et al. | |
| 5,178,147 A | 1/1993 | Ophir et al. | |
| 5,293,870 A | 3/1994 | Ophir et al. | |
| 6,246,895 B1* | 6/2001 | Plewes | 600/410 |
| 6,508,768 B1 | 1/2003 | Hall et al. | |
| 6,558,324 B1* | 5/2003 | Von Behren et al. | 600/440 |
| 2005/0215899 A1* | 9/2005 | Trahey et al. | 600/439 |
| 2006/0285731 A1* | 12/2006 | Jiang et al. | 382/128 |
| 2007/0106157 A1* | 5/2007 | Kaczkowski et al. | 600/438 |
| 2008/0097207 A1* | 4/2008 | Cai | 600/442 |
| 2009/0005682 A1 | 1/2009 | Fan et al. | |
| 2009/0105588 A1* | 4/2009 | Emelianov et al. | 600/438 |
| 2010/0234728 A1* | 9/2010 | Foley et al. | 600/439 |

OTHER PUBLICATIONS

U.S. Appl. No. 12/038,683, filed Feb. 27, 2008.
U.S. Appl. No. 12/174,011, filed Jul. 16, 2008.
U.S. Appl. No. 12/240,044, filed Sep. 29, 2008.

* cited by examiner

*Primary Examiner* — Brian Casler
*Assistant Examiner* — Joel Lamprecht

(57) ABSTRACT

Feedback of position is provided for high intensity focused ultrasound. The location of a beam from a HIFU transducer is determined using ultrasound imaging. The ultrasound imaging detects tissue displacement caused by a beam transmitted from the HIFU transducer. The displacement or information derived from the displacement may be used to detect and image the location of the beam. Separate transducers may be used for HIFU and imaging. The user aims the HIFU transmissions with feedback from ultrasound imaging of displacement of tissue.

21 Claims, 2 Drawing Sheets

FEEDBACK IN MEDICAL ULTRASOUND IMAGING FOR HIGH INTENSITY FOCUSED ULTRASOUND

FEDERALLY SPONSORED RESEARCH OR DEVELOPMENT

The U.S. Government has a paid-up license in this invention and the right in limited circumstances to require the patent owner to license others on reasonable terms as provided by the terms of contract no. HR 0011-08-3-0004 awarded by DARPA.

BACKGROUND

The present embodiments relate to ultrasound imaging. In particular, ultrasound imaging is used for feedback in high intensity focused ultrasound (HIFU).

HIFU is used to treat cancers, tumors, lesions, or other undesired tissue structures. Ultrasound energy heats the tissue sufficiently to necrotize the undesired tissue. The ultrasound energy is focused to avoid harming healthy tissue. Treatment with ultrasound may avoid invasive procedures, such as an operation or radio frequency ablation procedure.

Ultrasound imaging has been used to guide HIFU therapy. The imaging assists in focusing the therapy pulses on the undesired tissue. For example, a same array is used to image and transmit HIFU so that the HIFU is focused at the desired tissue. However, the HIFU may use a different array than used for imaging.

Attempts have also been made to monitor the thermal and biological changes of the tissue during these therapies. For example, ultrasound energy is used to measure thermal expansion coefficients (e.g., measure tissue expansion by speckle tracking), speed of sound in the tissue, or stiffness changes (e.g., strain imaging). However, these diagnostic based ultrasound tissue characterizations may not have sufficient signal-to-noise resolution or may not be clinically viable.

BRIEF SUMMARY

By way of introduction, the preferred embodiments described below include methods, instructions, and systems for providing feedback for high intensity focused ultrasound. The location of a beam from a HIFU transducer is determined using ultrasound imaging. The ultrasound imaging detects tissue displacement caused by a beam transmitted from the HIFU transducer. The displacement or information derived from the displacement may be used to detect and image the location of the beam. Separate transducers may be used for HIFU and imaging. The user aims the HIFU transmissions with displacement feedback from ultrasound imaging. Linked transducers or a common transducer may be used.

In a first aspect, a method is provided for providing feedback for high intensity focused ultrasound. An excitation is transmitted from a high intensity focused ultrasound transducer into tissue of a patient. Displacement of the tissue caused by the excitation is detected. An image of a beam profile of the excitation is generated as a function of the displacement.

In a second aspect, a computer readable storage medium has stored therein data representing instructions executable by a programmed processor for providing feedback for high intensity focused ultrasound. The storage medium includes instructions for determining a beam location for high intensity focused ultrasound therapy as a function of displacement of tissue, and generating an image of the beam location.

In a third aspect, a system is provided for providing feedback for high intensity focused ultrasound. A high intensity focused ultrasound transducer is operable to generate high intensity focused ultrasound therapy waveforms. An imaging transducer is movable separate from the high intensity focused ultrasound transducer. The imaging transducer is operable to receive signals responsive to a transmission from the high intensity focused ultrasound transducer. A receive beamformer is operable to output data representing spatial locations as a function of the receive signals. A processor is operable to estimate tissue displacement as a function of the output data and generate an image of a beam profile as a function of the tissue displacement. A display is operable to display the image of the beam profile.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Detecting the therapy beam or an emulation of the beam from displacement may account for phase aberrations and/or attenuation. Dose distribution may be better estimated using displacement imaging, such as elasticity, strain, or shear. The results of displacement imaging may be used to correct distribution of the therapy beam. The therapy transducer power and/or focus location may be adjusted based on the feedback. The HIFU transducer may be adjusted, such as aimed, based on the feedback.

Figure 1:
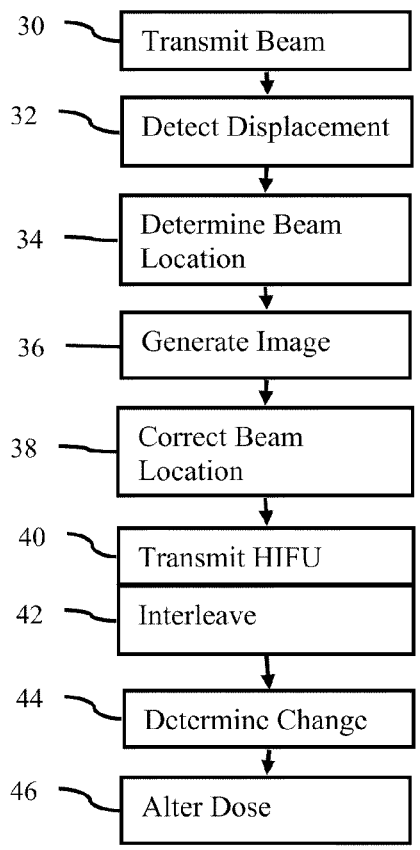
FIG. 1 is a flow chart diagram of one embodiment of a method for providing feedback for high intensity focused ultrasound.

FIG. 1 shows a method for providing feedback for high intensity focused ultrasound. The method is implemented by the system of FIG. 2 or a different system. Additional, different, or fewer acts may be provided. For example, acts 38-46 are not provided in some embodiments. The acts are performed in the order described or shown, but may be performed in other orders. For example, the beam location is corrected in act 38 prior to generating the image in act 36. As another example, acts 32-26 are repeated with act 40 as part of the interleaving of act 42.

In act 30, an excitation is transmitted from a high intensity focused ultrasound transducer. The excitation is acoustic energy. The acoustic energy is focused, resulting in a three-dimensional beam profile. The excitation is focused using a phased array and/or mechanical focus. The excitation may be unfocused in one dimension, such as the elevation dimension. The excitation is transmitted into tissue of a patient. The excitation is focused at a location for treatment, such as a tumor. However, due to acoustic effects, misalignment, or other factors, the beam may not properly overlap, cover, or even intersect the tissue location for treatment.

The excitation is generated as therapy excitation. Alternatively, the excitation emulates the therapy excitation. The high intensity focused ultrasound therapy waveform is emulated. A generally same focus, amplitude, frequency, or other characteristic as the therapy excitation is provided for the emulation. The emulation is used to substantially avoid therapeutic effect. For example, the amplitude, duration, or both are reduced as compared to a therapy waveform. "Substantially" avoiding therapeutic effect allows for generalization to a region, such as the region of treatment. A single point may be heated above a threshold level due to aberrations or focal distortion, but the treatment region overall avoids therapeutic effect from the emulation. Avoiding therapeutic effect may be avoiding heating to the point of altering the tissue or creating cavitations. For example, biological effects may include hyperthermia at tissue temperature of about 41-45° C., protein denaturation at temperatures above 45° C., and tissue necrosis at temperatures above 50° C. Tissue stiffness may be affected even at temperatures below 45° C. At temperatures above 45° C., increases in viscosity and/or stiffness may occur. At temperatures above 50° C., the tissue may have a high stiffness and/or high attenuation.

In act 32, displacement of the tissue is detected. The excitation causes displacement of the tissue. The displacement may be caused by a longitudinal wave. The displacement may alternatively or additionally be caused by a shear wave.

The displacement is detected with ultrasound scanning. The locations, magnitude, timing, and/or other characteristic of the displacement are detected. For example, locations associated with a threshold amount of displacement caused by the emulation are detected.

To detect the displacement, ultrasound energy is transmitted to the tissue undergoing displacement and reflections of the energy are received. The transmission and reception are performed multiple times to determine change due to displacement. Any transmission and reception sequence may be used. The displacement is detected from the differences for each spatial location. For example, the velocity, variance, shift in intensity pattern (e.g., speckle tracking), or other information is detected from the received data as the displacement.

Any now known or later developed displacement imaging may be used. For example, diagnostic pulses, such as having an intensity and duration below the regulated levels for diagnostic ultrasound, are transmitted. For example, pulses with 1-5 cycle durations are used with an intensity of less than 720 mW/cm$^2$. Pulses with other intensities may be used, such as pulses with less than 1000 mW/cm$^2$. The ultrasound transmission is focused at a region including the tissue to be treated. The transmission may cover one or more scan lines. For example, a wide beam width transmit pulse is used for receiving along two or more receive scan lines with a plane or volume distribution. Alternatively, a single receive beam is formed in response to a transmit. A region may be sequentially scanned. One or more measurements are performed for each receive scan line.

Two or more, such as 2-10, pulses are transmitted to a same location for each measurement or for combining measurements. Alternatively, a single pulse may be transmitted for each measurement. Where the therapeutic intensity and time since cessation are known, a single pulse may be used and compared to pre-emulation or excitation measurement to determine a change in position.

After cessation of the excitation emulating the therapeutic ultrasound, the tissue moves to a relaxed position. Echoes from the multiple relatively low diagnostic imaging pulses are received. The echoes are used to generate one or more images to identify locations with displacement caused by the therapy-associated excitation.

The echoes are detected using B-mode or Doppler detection. Using B-mode data, the data from multiple pulses is correlated. The correlation is one, two or three-dimensional. For example, correlation along a scan line away and toward the transducer is used. Any now known or later developed correlation may be used, such as cross-correlation, pattern matching, or minimum sum of absolute differences. Tissue structure and/or speckle are correlated. Using Doppler detection, a clutter filter passes information associated with moving tissue. The velocity of the tissue is derived from multiple echoes. The velocity is used to determine the displacement towards or away from the transducer. Alternatively, the relative or difference between velocities at different locations may indicate strain or displacement.

The amount of displacement represents regions subjected to force from the excitation associated with HIFU. The time associated with a particular displacement allows estimation of the decay curve. By measuring the displacement as a function of time, the decay of strain from cessation of the excitation may be measured. Displacement alone or any displacement characteristic of the decay may be measured.

In other embodiments, strain or elasticity imaging is used. The displacement of tissue is determined as a function of time. The displacement may be measured from tissue data, such as B-mode ultrasound data. Correlation, cross-correlation, minimum sum of absolute differences or other similarity measure is used to determine the displacement between scans. The displacements are determined along one, two, or three dimensions. In one embodiment, any one or more of the methods or systems disclosed in U.S. Pat. Nos. 5,107,837; 5,293,870; 5,178,147; 6,508,768 or 6,558,324, the disclosures of which are incorporated herein by reference, are used to generate elasticity frames of data or images as the strain information. Other methods of measuring strain may be used. The displacement may be measured by determining tissue velocity and/or acceleration.

Based on one (e.g., velocity), two (B-mode correlation), or more (e.g., average displacement) scans, a strain field is determined. The strain field represents strain at the different locations. A displacement field or a strain rate field may be used in other embodiments. Other measurements may be used to represent strain or displacement, such as velocity.

Figure 3:
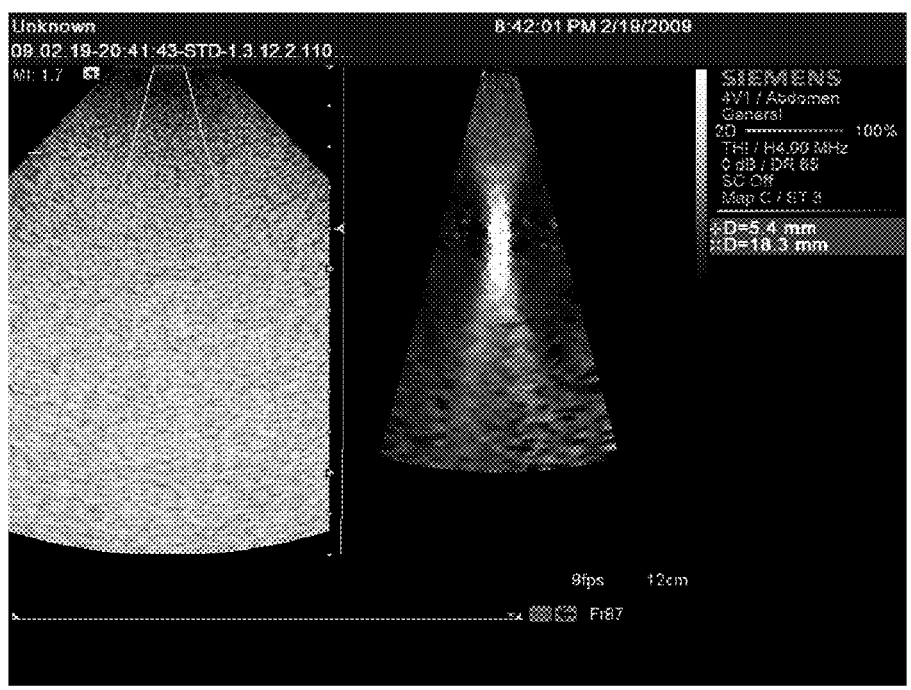
FIG. 3 is a medical image showing a tissue region and a detected beam profile.

The displacement is detected over any size region. In one embodiment, the displacement is detected in a region of interest likely to include the tissue to be treated, such as about ⅓ to ½ the complete scan region for B-mode imaging. FIG. 3 shows one embodiment where the image on the left shows a region of interest box for displacement imaging. Greater, lesser, or no region of interest may be used, such as detecting displacement over the entire imaging region. Narrower regions of interest may allow for displacement detection with fewer repetitions of transmitting the excitation waveform associated with HIFU. Depending on the number of receive beams that may be formed and the sample density, none, one, or more repetitions may be used. Full sampling, such as sampling displacement on every B-mode sample location, may be used. Greater or lesser (e.g., sparse) sampling of displacement relative to the B-mode scan grid may be used.

In one embodiment, shear waves are detected in addition to or as an alternative to longitudinal waves. The excitation forms a beam, which generates a shear wave at spatial locations. Where the beam is sufficiently strong, a shear wave is generated. The shear wave propagates through tissue more slowly than the longitudinal wave along the acoustic wave emission direction. The shear wave propagates various directions, including a direction perpendicular to the direction of the applied stress. The displacement of the shear waves is greater at locations corresponding to the excitation beam.

Ultrasound data is obtained. At least some of the ultrasound data is responsive to a shear wave. A region of interest is monitored to detect the shear wave. The region of interest is any size, such as 6 mm in lateral and 10 mm in axial. This detection region is monitored by ultrasound. For example, B-mode scans are performed to detect tissue displacement caused by the shear wave. Doppler, color flow, or other ultrasound mode may be used to monitor for the shear wave.

The monitoring is performed for any number of scan lines. For example, four receive beams are formed in response to each transmission. After transmitting the excitation to generate the shear wave, B-mode transmissions are performed repetitively along a single scan line and receptions along four adjacent scan lines. Any number of repetitions may be used, such as about 120 times. Some of the ultrasound data, such as at the beginning or end of the repetitions, may not be responsive to the shear wave. In other embodiments, only a single receive beam or other numbers of receive beams are formed in response to each transmission.

As the shear wave propagates through the scan lines, the B-mode intensity may vary. For the monitored scan lines, a sequence of data is provided representing a time profile of tissue motion resulting from the shear wave. For example, data from a plurality of spatial locations (e.g., along the scan lines) is correlated as a function of time. Any elasticity detection may be used. For each depth or spatial location, a correlation over a plurality of depths or spatial locations (e.g., kernel of 64 depths with the center depth being the point for which the profile is calculated) is performed. Two or three-dimensional displacement in space may be used. One-dimensional displacement along a direction different than the scan lines or beams may be used.

The spatial offset with the highest or sufficient correlation at a given time indicates the amount of displacement. Displacements are determined for a given location at different times. The temporal profile for a given location indicates detection of the shear wave. The profile is examined for a non-noise or single instance of variation. A peak in the profile, with or without temporal low pass filtering, indicates the passing of the shear wave front. The greatest displacement is selected, but the average or other displacement statistic may be used. The maximum shear at a given location is detected. Alternatively, an average or other shear is detected.

To monitor a larger region, additional receive beams are formed in response to the monitoring transmit beam. Alternatively, another shear wave is generated and the transmit beams and receive beams are provided at a different distance from the shear wave generation point. In the 6 mm×10 mm example above, 36 receive scan lines may be provided. At four receive beams per transmit beam, the process is repeated for different lateral spacing nine times. For each receive beam location, a time profile of motion information is provided, represented by the ultrasound data. Transmissions along different scan lines to monitor a same shear wave are avoided during formation of the temporal profile to provide higher temporal resolution, but interleaved or shifting scanning positions may be provided.

The discussion above is for one depth. The sampling may be arranged to provide one gate covering the entire axial extent of the region of interest. In another embodiment, samples are obtained at multiple depths for each receive beam. A separate time profile is provided for each axial depth as well as lateral location. Any number of depths may be used, such as about 200 for 5 mm or 400 for 10 mm.

Ultrasound data representing different locations in the region of interest is obtained. The ultrasound data is obtained in real-time with the scanning or obtained from a memory. For each location, the motion information represents the response at different times. Other scanning, monitoring, or techniques may be used to obtain ultrasound data to estimate shear magnitude.

The tissue may change over time, such as where the detection of the shear wave is interleaved with actual application of the therapy HIFU. The stiffness of the tissue may increase in the treatment locations. This change in stiffness may alter the detected magnitude of the shear. Shear velocity and/or modulas or other complex representation of shear may be used to minimize or avoid the effects of changes in the tissue. Shear velocity may be preferred where modulus in otherwise not available or difficult to determine. The absorption coefficient may be assumed (e.g., 0.5, 0.6, 0.8 or other value) depending on the tissue being treated. The shear velocity and/or modulas may be determined, at least in part, based on the pressure and absorption coefficient. The pressure applied is known from the transmitted excitation and consideration of attenuation.

Shear velocity is detected for the different spatial locations of the tissue. For each location, the displacement as a function of time is determined. The shear velocity is obtained by determining a time from generation of the shear wave until detection of the shear wave at a different location. The time and distance to the location determine the velocity. The distance is known from the scan line spacing (i.e., the transmit beam position for generating the shear wave and the receive beam position for detecting the shear wave). The time is known from the relative time between generation and detection of the shear wave.

Other techniques may be used to detect the peak in the profile. For example, a regression is applied. Since the shear wave velocity is linear, a robust linear regression with automated outlier detection may indicate the shear wave velocity. The ultrasound data for all of the sample points in the region of interest is plotted for distance as a function of time or by time and distance. The linear regression is applied to the plot or data, providing a line fit to the data. The slope of the line indicates the shear wave velocity.

Other approaches may be used. For example, data from different times is correlated to detect the shift in tissue caused by the shear wave. As another example, a feature is extracted from the temporal profiles. Principle component decomposition may be used. A correlation between the different temporal profiles is performed. The lag associated with the different distances for the different temporal profiles provides the velocity. Alternatively, a wavelet analysis may be performed. A wavelet transform is applied to the temporal profiles to identify a peak corresponding to the shear wave. A velocity value is identified from the travel time of the peak to each spatial location.

All the peak travel time data from the full region of interest may be used together, such as in linear regression. Only a subset of the data may be used, such as using data for one depth for feature extraction or regression. Shear velocities may be calculated for each location in the region of interest. Alternatively, a spatial representation of shear wave velocity variance within the region of interest may be provided.

In approaches by others, any modulus or shear value may be estimated. Tissue modulus values represent the hardness or stiffness at the locations. For example, the shear modulus of tissue is estimated. In alternative embodiments, Young's modulus is estimated. In other embodiments, other shear values are estimated, whether quantitative or qualitative.

The shear modulus is given by $g=\rho v^2$, where $\rho$ is density, and $v$ is estimated shear velocity. In one embodiment, the tissue moduli or shear information, such as the shear modulus, is determined as a function of the strain or displacement and the moduli or shear information. For example, the shear modulus for each sample location is determined by iteratively solving a diffusion equation. Assuming a Poisson's ratio of 0.5 or using a known Poisson's ratio, the shear modulus at different locations is calculated iteratively as a function of the strain field at different times or under different stress for the different locations and the shear modulus.

In act 34, a beam location for the HIFU is determined using the displacement of tissue information. Locations associated with sufficient magnitude of displacement, shear, shear velocity, or shear modulus are identified. Locations where the displacement is relatively high are identified by applying a threshold. Relative is to a threshold or other values, which are preprogrammed or adapt to a given data set. The threshold may be normalized, such as a threshold based on data at spatial locations spaced away from the likely location of the beam. As another example, an average displacement across a region of interest is determined. Locations associated with a maximum displacement greater than the average indicate beam locations. Alternatively, a preprogrammed or other threshold is applied. In other or additional embodiments, no threshold is applied, or a noise threshold is used. The range of displacements are mapped to display values such that low or no displacement regions are at one end of the dynamic range and the highest displacements are at the other end of the dynamic range. Linear or non-linear mapping may be used.

The displacement data may or may not be spatially filtered prior to application of the threshold. The displacements may be low pass filtered after application of the threshold.

In act 36, image data is generated as function of the displacement. For example, the image represents the beam profile of the excitation. The beam profile corresponds to locations with sufficient displacement. The image shows the location of the beam, including the spatial distribution of the beam. The image represents the spatial extent of the beam profile in one or more dimensions. FIG. 3 shows an image on the right side of the beam. Brighter or more intense locations correspond to greater displacement. The image may be filtered, such as low pass filtered.

The displacement data is in a display format or may be scan converted into a display format. The displacement data is color or gray scale data, but may be data prior to mapping with gray scale or color scale. The information may be mapped linearly or non-linearly to the display values.

The image represents the displacement information, such as shear or moduli (e.g., the shear moduli) for the different locations. Where the values are determined for all of the grid points in a region of interest or field of view, the pixels of the display represent the beam for that region. The display grid may be different from the scan grid and/or grid for which displacements are calculated. Color, brightness, luminance, hue, or other characteristic is modulated as a function of the displacement.

The image may include other data. For example, B-mode or other data representing tissue, fluid, or contrast agents in the same region is included. The displacement data is used for an overlay of or combination with the other data. The other data assists the user in determining the location of the beam relative to the tissue to be treated.

In an alternative embodiment, the image is generated as a function of the displacement and a beam profile model. The displacement may be noisy. A model of the therapy beam is provided. The model may be generated using empirical information or theoretical calculation. The beam profile model is created as an inverse problem to determine the likely distribution of the beam profile. The spatial and temporal displacement may be formulated based on the beam profile model. Given the measured displacements and models, a representation of the best fit or least square fit of the measurements to the model is determined. The fit representation is used for generating the image, such as a graphic overlay sized and shaped based on the fit. The beam profile represented by the image is reconstructed by fitting a model to the measured displacements.

In act 38, the beam profile is corrected as a function of acoustic propagation. The measured displacement is or is not corrected for depth dependent attenuation of the applied stress. As pressure propagates through tissue, the pressure attenuates. Less motion or displacement is caused at locations spaced further from the source of pressure (depth relative to the source) due to the attenuation. The displacement is adjusted to account for the attenuation, providing more normalized displacements or strain at different depths.

The correction is linear as a function of distance away from the point or region of the source (e.g., transducer) of stress. Non-linear correction may be used, such as based on tissue models or different types of tissue. The linear or non-linear function is assumed, based on empirical data, or is based on a propagation model. For acoustic force, the attenuation of sound in tissue as a function of distance and frequency is corrected. In other embodiments, no correction for attenuation and/or frequency is performed.

In act 40, high intensity focused ultrasound therapy waveforms are transmitted. High voltage waveforms are applied to the high intensity focused ultrasound transducer, which generates the HIFU therapy waveforms in the acoustic domain. The HIFU pulse is focused using a phased array or mechanical focus and provides the high intensity acoustic energy to tissue at a focal or beam location. The therapeutic ultrasound pulse has a plurality of cycles at any desired frequency. In one embodiment, the therapeutic pulse lasts for a fraction of a second to seconds at an ultrasound frequency, such as 500 KHz-20 MHz. Any peak intensity may be provided, such as 100 or more watts per square centimeter, 500 or more watts per square centimeter, 1000-2000 watts per square centimeter, or about 1000 watts per square centimeter. Any now known or later developed therapeutic waveform with any intensity, frequency, and/or number of cycles may be used. The waveform is continuous or intermittent.

The therapeutic ultrasound pulse treats the tissue by generating heat at the desired tissue location. The intensity also generates stress on the tissue. The pulse pushes the tissue towards and away from the transducer with negative and positive acoustic pressures. For a sufficiently long therapeutic pulse, a substantially constant strain on the tissue is created. The strain, $\epsilon$, is a function of the tissue stiffness, E, the viscosity, $\eta$, and the stress from HIFU radiation force. The steady state stress during the therapeutic pulse is proportional to the ratio of average HIFU intensity, I, to the speed of sound in the tissue, c.

The HIFU waveforms also generate biomechanical changes that can be detected. The thermal effects of the therapy acoustic energy may cause changes in volume due to thermal expansion, in the speed of sound (c), in tissue stiffness (E), and/or in the viscosity (η) of fluids in the tissue. The therapy acoustic energy may also induce mechanical effects, such as radiation pressure, streaming, and/or cavitations. The biological effects may include hyperthermia at tissue temperature of about 41-45° C., protein denaturation at temperatures above 45° C., and tissue necrosis at temperatures above 50° C. Tissue stiffness may be affected even at temperatures below 45° C. At temperatures above 45° C., increases in viscosity and/or stiffness may occur. At temperatures above 50° C., the tissue may have a high stiffness and/or high attenuation.

Before subjecting the tissue to treatment, the position of the HIFU beam is determined from the image generated in act 36. The user may reposition the transducer, a focal location, or change other settings to position the beam over the tissue to be treated while minimizing healthy tissue subjected to the HIFU. Automated positioning may be used in other embodiments, such as where the tissue to be treated is determined using computer assisted diagnosis. After positioning the beam as desired, the HIFU is transmitted in act 40.

The HIFU may be continuous or sporadic. Any treatment regimen may be used. During ongoing treatment or in between different fractions of the treatment, the imaging of act 36 may be performed. The therapy waveforms of act 40 are interleaved with the imaging of act 36. The imaging of act 36 is performed using the transmitting of act 30, the detection of act 32, and the determination of act 34. The HIFU treatment ceases while the beam location is determined. Alternatively, the HIFU transmissions of act 40 are used as the excitation for detecting displacement in act 32. The HIFU may cease for detection of displacement, or the displacement due to the HIFU waveforms is used. In another alternative, the HIFU is performed at one frequency or coding, and the transmission of the excitements and corresponding reception are performed at a different frequency or coding, allowing operation at the same time given pre-treatment tissue position information. The interleaving allows user or system positioning of the HIFU beam on an on-going basis. If the patient or transducer shifts position, the beam may be altered to treat the appropriate tissue. If the speed of sound in the tissue changes due to the treatment, the beam may be altered to treat the appropriate tissue.

In act 44, a change in the tissue from high intensity focused ultrasound therapy is determined. For example, the change in the displacements is determined. HIFU may cause the tissue to be less elastic or stiffer. Ablation, collagen denaturization, coagulation, or other effects may alter the shear velocity or other characteristic. The amount of displacement given a same or known but different stress may be determined. The amount or magnitude of displacement may be measured. Any measurement may be used, such as a median or mean of change in displacement for a region. Changes in shear, strain, elasticity, modulus, velocity, or other tissue characteristic may be measured.

The change is determined by the user or by the system. For example, a quantity is determined. As another example, the user detects the change based on one or more images.

The change may be used for feedback control of dosing. In act 42, the application of HIFU in act 40 may be altered or ceased based on the change. The dosage of the high intensity focused ultrasound therapy is altered as a function of the change. To minimize damage to healthy tissue, the HIFU intensity or duration may be reduced where sufficient treatment has occurred. The change in tissue indicates sufficiency of treatment. To avoid ineffective treatment, the HIFU intensity or duration may be increased where insufficient treatment has occurred, as reflected by less than expected change.

Figure 2:
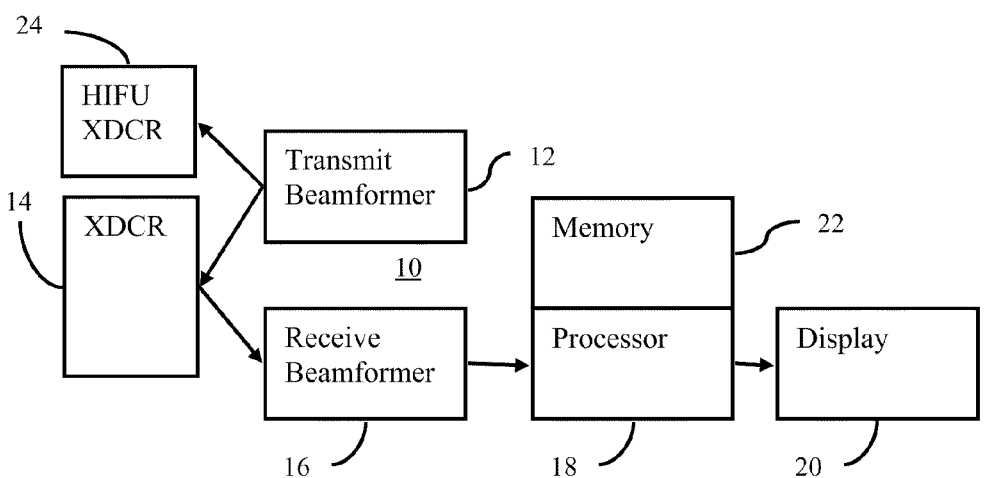
FIG. 2 is a block diagram of one embodiment of a system for providing feedback for high intensity focused ultrasound.

FIG. 2 shows one embodiment of a system 10 for providing feedback for high intensity focused ultrasound. The system 10 implements the method of FIG. 1 or other methods. The system 10 includes a transmit beamformer 12, a transducer 14, a receive beamformer 16, an image processor 18, a display 20, a memory 22, and a HIFU transducer 24. Additional, different or fewer components may be provided. For example, a user input is provided for manual or assisted alteration of a beam profile (e.g., selection of frequency, focal depth, scan line angle, aperture, focal location, and/or apodization). The system 10 is a medical diagnostic ultrasound imaging system. In alternative embodiments, the system 10 is a personal computer, workstation, PACS station, or other arrangement at a same location or distributed over a network for real-time or post acquisition imaging.

The transmit beamformer 12 is an ultrasound transmitter, memory, pulser, analog circuit, digital circuit, or combinations thereof. The transmit beamformer 12 is operable to generate waveforms for a plurality of channels with different or relative amplitudes, delays, and/or phasing. Upon transmission of acoustic waves from the transducer 14 in response to the generated waves, one or more beams are formed. A sequence of transmit beams are generated to scan a two or three-dimensional region. Sector, Vector®, linear, or other scan formats may be used. The same region is scanned multiple times. For flow or Doppler imaging and for strain imaging, a sequence of scans is used. In Doppler imaging, the sequence may include multiple beams along a same scan line before scanning an adjacent scan line. For strain imaging, scan or frame interleaving may be used (i.e., scan the entire region before scanning again). In alternative embodiments, the transmit beamformer 12 generates a plane wave or diverging wave for more rapid scanning.

The same transmit beamformer 12 is shown for generating HIFU and/or emulation waveforms with the HIFU transducer 24 and displacement detection with the imaging transducer 14. In alternative embodiments, different transmit beamformers 12 are provided for imaging displacement and therapy. For example, a separate therapy system is used. The transducer 14 and transmit beamformer 12 are used to image displacement for operating the separate therapy system. In another alternative, the same transducer 14 is used for both detecting displacement and applying therapy. One or more elements are used for both therapy and diagnostic transmissions.

The high intensity focused ultrasound transducer 24 generates high intensity focused ultrasound therapy waveforms. The HIFU transducer 24 is an array for generating acoustic energy from electrical waveforms. One-dimensional or multidimensional arrays may be used. Alternatively, a single element with a mechanical focus is used. For an array, relative delays focus the acoustic energy. A given transmit event corresponds to transmission of acoustic energy by different elements at a substantially same time given the delays. The transmit event provides a pulse of ultrasound energy for treating the tissue. Alternatively, a mechanical focus is provided for the array. Any now known or later developed therapy transducer 24 may be used.

In one embodiment, the HIFU transducer 24 is separate from the imaging transducer 14. The imaging transducer 14 is moveable separate from the HIFU transducer 24. Imaging is used to determine the therapy location. The imaging transducer 14 receives echo signals responsive to one or more transmissions from the HIFU transducer 24. For example, signals responsive to an emulation of therapy waveforms are received. Alternatively or additionally, both transducers 14, 24 include spatial registration systems, such as magnetic position sensors. The transducers 14, 24 are not connected together, but may be, such as being positioned in a same housing.

The transducer 14 is a 1-, 1.25-, 1.5-, 1.75- or 2-dimensional array of piezoelectric or capacitive membrane elements. The transducer 14 includes a plurality of elements for transducing between acoustic and electrical energies. Receive signals are generated in response to ultrasound energy (echoes) impinging on the elements of the transducer 14. The elements connect with channels of the transmit and receive beamformers 12, 16.

The receive beamformer 16 includes a plurality of channels with amplifiers, delays, and/or phase rotators, and one or more summers. Each channel connects with one or more transducer elements. The receive beamformer 16 applies relative delays, phases, and/or apodization to form one or more receive beams in response to each transmission. The receive beamformer 16 outputs data representing spatial locations using the receive signals. Relative delays and/or phasing and summation of signals from different elements provide beamformation. In alternative embodiments, the receive beamformer 16 is a processor for generating samples using Fourier or other transforms.

The receive beamformer 16 may include a filter, such as a filter for isolating information at a second harmonic or other frequency band relative to the transmit frequency band. Such information may more likely include desired tissue, contrast agent, and/or flow information. In another embodiment, the receive beamformer 16 includes a memory or buffer and a filter or adder. Two or more receive beams are combined to isolate information at a desired frequency band, such as a second harmonic, cubic fundamental or other band.

The receive beamformer 16 outputs beam summed data representing spatial locations. Data for a single location, locations along a line, locations for an area, or locations for a volume are output. Dynamic focusing may be provided. The data may be for different purposes. For example, different scans are performed for B-mode or tissue data than for displacement. Alternatively, the B-mode data is also used to determine displacement.

The processor 18 is a B-mode detector, Doppler detector, pulsed wave Doppler detector, correlation processor, Fourier transform processor, application specific integrated circuit, general processor, control processor, image processor, field programmable gate array, digital signal processor, analog circuit, digital circuit, combinations thereof or other now known or later developed device for detecting and processing information for display from beamformed ultrasound samples.

In one embodiment, the processor 18 includes one or more detectors and a separate processor. The separate processor is a control processor, general processor, digital signal processor, application specific integrated circuit, field programmable gate array, network, server, group of processors, data path, combinations thereof or other now known or later developed device for determining displacement, and calculating tissue properties. For example, the separate processor performs any combination of one or more of the acts shown in FIG. 1.

The processor 18 estimates tissue displacement as a function of beamformed samples. Any type of displacement may be estimated. For example, the processor 18 detects shear wave displacement information. In another example, the processor 18 applies modulus, or shear velocity estimation. The processor 18 determines information as a function of the output data from the receive beamformer 16.

The processor 18 outputs image or display values mapped from the tissue properties to the display 20. For example, the maximum displacement, shear velocity, shear modulus, or other value is determined for each location. The magnitude of the values modulates the color, hue, brightness, and/or other display characteristic. An image of the beam profile represented as tissue displacement in generated from the modulated display values. The image may be shown alone or overlaid or combined with other images (e.g., B-mode image).

FIG. 3 shows an image of a beam profile. The brighter regions correspond to greater displacement. The displacement values are based on displacement due to an emulation of the HIFU therapy waveforms or the therapy waveforms themselves. The emulation or actual therapy waveforms are transmitted from the HIFU transducer 24 so that the beam position corresponds to the treatment beam. The image represents a spatial extent of the beam profile and/or relative position in a patient.

In one embodiment, the processor 18 is a control processor. The processor 18 controls use of the HIFU therapy waveforms. Based on detected changes in the tissue displacement, the processor 18 determines whether to cease the therapy prior to a scheduled end.

For determining displacement, data from a plurality of scans or measurements may be acquired and stored. The data is stored in the memory 22 or a different memory. Data from one or more stages of processing is stored, such as radio frequency data, channel data, beam sum data, detected data, strain data, shear data, modulus data, shear modulus data, and/or calculated values.

The processor 18 operates pursuant to instructions stored in the memory 22 or another memory. The processor 18 is programmed for providing feedback for high intensity focused ultrasound. The memory 22 is a computer readable storage media. The instructions for implementing the processes, methods and/or techniques discussed herein are provided on the computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing, and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

The display 20 is a CRT, LCD, projector, plasma, or other display for displaying two-dimensional images or three-dimensional representations. The display 20 displays one or more images representing the HIFU beam profile. The spatial distribution of displacement associated with HIFU is shown in the image.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for providing feedback for high intensity focused ultrasound, the method comprising:
    transmitting an excitation from a high intensity focused ultrasound transducer into tissue of a patient;
    detecting displacement of the tissue caused by the excitation; and
    displaying an image of a beam profile of the excitation as a function of the displacement.

2. The method of claim 1 further comprising:
    transmitting a high intensity focused ultrasound therapy waveform with the high intensity focused ultrasound transducer;
    wherein transmitting the excitation comprises transmitting the excitation as an emulation of the high intensity focused ultrasound therapy waveform, the emulation having a different amplitude, duration, or both amplitude and duration than the therapy waveform.

3. The method of claim 2 wherein the emulation substantially avoids therapy heating and cavitation, and the therapy waveform provides heating or cavitation.

4. The method of claim 1 wherein detecting displacement of the tissue comprises transmitting additional ultrasound to the tissue and receiving reflections from the transmitting of the additional ultrasound, the transmitting the additional ultrasound and receiving being performed multiple times, and detecting the displacement from the reflections from the multiple receiving.

5. The method of claim 1 wherein detecting displacement of the tissue comprises detecting shear waves caused by the excitation.

6. The method of claim 5 wherein detecting shear waves comprises detecting shear velocity or modulus.

7. The method of claim 1 wherein generating the image of the beam profile of the excitation comprises generating a multidimensional image showing a spatial extent and location of the beam profile of the excitation within the tissue.

8. The method of claim 1 further comprising:
    correcting the beam profile as a function of a nonlinear acoustic propagation.

9. The method of claim 1 further comprising:
    transmitting high intensity focused ultrasound therapy waveforms with the high intensity focused ultrasound transducer; and
    interleaving the therapy waveforms with repetitions of the transmitting the excitation and detecting.

10. The method of claim 1 further comprising:
    determining a change in the tissue from high intensity focused ultrasound therapy as a function of the displacements; and
    altering dosage of the high intensity focused ultrasound therapy as a function of the change.

11. The method of claim 1 wherein generating the image of the beam profile comprises reconstructing the beam profile as a function of the displacement and a beam profile model.

12. In a non-transitory computer readable storage medium having stored therein data representing instructions executable by a programmed processor for providing feedback for high intensity focused ultrasound, the storage medium comprising instructions for:
    determining a beam location for high intensity focused ultrasound therapy as a function of displacement of tissue; and
    generating an image of the beam location.

13. The non-transitory computer readable storage medium of claim 12 further comprising transmitting a high intensity focused ultrasound therapy waveform, wherein determining comprises transmitting an emulation of the high intensity focused ultrasound therapy waveform, the emulation having a different amplitude, duration, or both amplitude and duration than the therapy waveform, the emulation substantially avoiding therapy heating and cavitation, and determining the displacement with ultrasound scanning, locations of displacement being caused by the emulation.

14. The non-transitory computer readable storage medium of claim 12 wherein determining the beam location as a function of displacement of the tissue comprises detecting shear waves caused by a beam corresponding to the beam location.

15. The non-transitory computer readable storage medium of claim 12 wherein determining the beam location comprises determining a shear velocity or modulus for different spatial locations of the tissue, the beam location corresponding to spatial locations with greater shear velocity or modulus than other spatial locations.

16. The non-transitory computer readable storage medium of claim 12 wherein generating the image of the beam location comprises generating a multidimensional image showing a spatial extent of a beam profile within the tissue.

17. The non-transitory computer readable storage medium of claim 12 further comprising instructions for correcting the beam location as a function of a nonlinear acoustic propagation.

18. The non-transitory computer readable storage medium of claim 12 further comprising instructions for determining a change in the tissue from the high intensity focused ultrasound therapy as a function of the displacements, and altering dosage of the high intensity focused ultrasound therapy as a function of the change.

19. A system for providing feedback for high intensity focused ultrasound, the system comprising:
    a high intensity focused ultrasound transducer operable to generate high intensity focused ultrasound therapy waveforms;
    an imaging transducer, movable separate from the high intensity focused ultrasound transducer, operable to receive signals responsive to a transmission from the high intensity focused ultrasound transducer;
    a receive beamformer operable to output data representing spatial locations as a function of the receive signals;
    a processor operable to estimate tissue displacement as a function of the output data and generate an image of a beam profile as a function of the tissue displacement; and
    a display operable to display the image of the beam profile.

20. The system of claim 19 wherein the transmission comprises an emulation of the high intensity focused ultrasound therapy waveforms, wherein the tissue displacement comprises a shear wave displacement, wherein the beam profile is for the emulation, and wherein the processor is configured to generate the as representing a spatial extent of the beam profile and relative position in a patient.

21. The system of claim 19 wherein the processor is operable to control use of the high intensity focused ultrasound therapy waveforms, the use controlled as a function of a change detected from the tissue displacement.

* * * * *